United States Patent [19]

Mathias

[11] 4,080,484
[45] Mar. 21, 1978

[54] PHOTOCURABLE IMIDIZABLE POLYENE-POLYTHIOL COMPOSITIONS, METHOD OF COATING THEREWITH AND COATED ARTICLES

[75] Inventor: Eckart Mathias, Catonsville, Md.

[73] Assignee: W. R. Grace & Co., New York, N.Y.

[21] Appl. No.: 753,750

[22] Filed: Dec. 23, 1976

[51] Int. Cl.² ............................................. B05D 3/06
[52] U.S. Cl. ............................. 428/379; 204/159.19; 260/78 SC; 260/78 TF; 260/78 UA; 427/44; 427/54; 427/120; 427/358; 427/372 R; 427/434 D; 428/419
[58] Field of Search ......... 260/78 TF, 78 UA, 78 SC; 204/159.19; 427/44, 54, 117, 120, 358, 372 R, 434 D; 428/379, 419

[56] References Cited

U.S. PATENT DOCUMENTS

| | | |
|---|---|---|
| 3,483,104 | 12/1969 | D'Alelio ..................... 260/78 UA |
| 3,663,651 | 5/1972 | Traut ........................... 260/78 TF |
| 3,845,018 | 10/1974 | Bilow et al. .................. 260/78 UA |
| 3,897,395 | 7/1975 | D'Alelio ..................... 260/78 TF |
| 3,993,630 | 11/1976 | Darmory et al. ............ 260/78 TF |
| 3,998,786 | 12/1976 | D'Alelio ..................... 260/78 TF |

*Primary Examiner*—John H. Newsome
*Attorney, Agent, or Firm*—Richard P. Plunkett; William W. McDowell, Jr.

[57] ABSTRACT

This invention relates to polyenes containing at least two ethylenically unsaturated bonds per molecule formed by reacting in substantially stoichiometric amounts, (1) a primary diamine, (2) a member of the group consisting of a benzenoid-containing dianhydride, acid anhydride and anhydride acid halide and (3) an ethylenically unsaturated alcohol. The thus formed amide-acid polyene either per se or after being cured in combination with a polythiol in the presence of a free radical generator will, upon heating, imidize.

29 Claims, No Drawings

PHOTOCURABLE IMIDIZABLE POLYENE-POLYTHIOL COMPOSITIONS, METHOD OF COATING THEREWITH AND COATED ARTICLES

This invention relates to a polyene composition, procedures for making same and cured products resulting therefrom. More particularly, this invention relates to an amide-acid polyene, a method of preparing same, as well as curing the polyene with a polythiol in the presence of a free radical generator to solid, crosslinked, solvent-insoluble materials, which on heating will imidize resulting in improved high temperature properties.

It is known that polyenes are curable by polythiols in the presence of free radical generators such as actinic radiation to solid polythioether-containing resinous or elastomeric products. See U.S. Pat. No. 3,661,744. However, high temperature characteristics of the cured product are somewhat lacking due to the aliphatic nature of the polyenes employed. For example, in the wire coating field present day commercially available polyenes because of their aliphatic structure fail the NEMA specified heat shock and cut-through tests at the upper temperature limits at which these tests are run, thereby negating their operability for this end use. Thus, a coating having good high temperature properties after curing is a desirous element.

In accordance with this invention.
An amide-acid polyene of the formula:

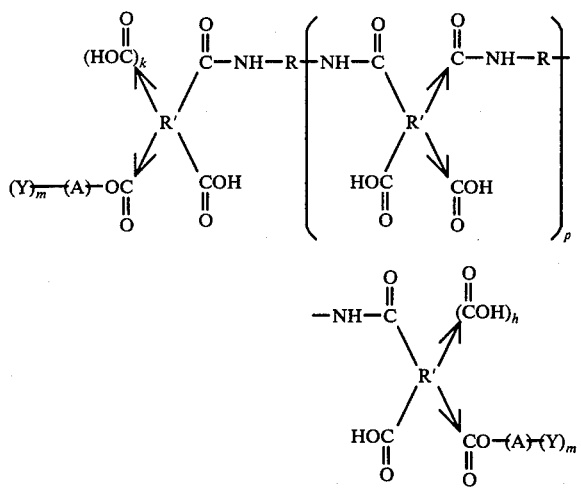

wherein → denotes isomerism, R is a divalent organic moiety remaining after a primary diamine has reacted to form amide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of $-CR''=CH_2$, $-O-(CH_2)_d-CR''=CH_2$ and $$-\overset{O}{\underset{\|}{C}}OCH_2CR''=CH_2$$

R'' is hydrogen or methyl; $k$ and $h$ are 0 or 1; $m$ and $d$ are 1 to 10; and $p$ is 0 to 10 is obtained by reacting in substantially stoichiometric amounts (1) a primary diamine, (2) a member of the group consisting of a benzoid-containing dianhydride, acid anhydride and anhydride acid halide and (3) an ethylenically unsaturated alcohol.

The thus formed polyene, on heating, can be imidized per se to form a polyene with improved high temperature properties of the formula:

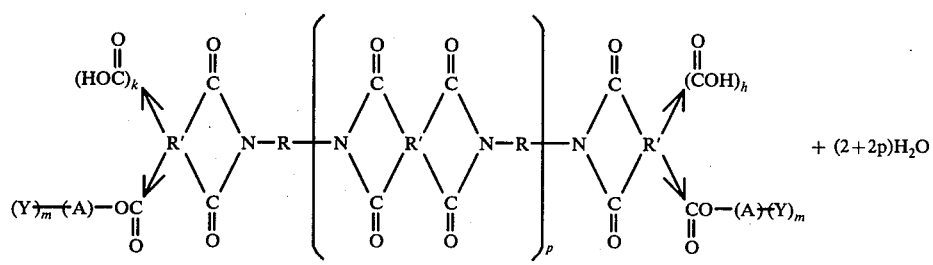

$+ (2+2p)H_2O$ wherein R is a divalent organic moiety remaining after the di-secondary amide has reacted with adjacent carboxylic acid groups to form imide linkages and R', R'', A, Y, $k$, $h$, $m$, $d$ and $p$ are as hereinbefore set forth. Additionally, the amide-acid polyene in combination with a polythiol on exposure to a free radical generator forms a cured polythioether which, upon heating, will imidize resulting in improved high temperature properties. This polyene and polythiol mixture is a highly reactive composition which is capable of being photocured when exposed to actinic radiation in the presence of a U.V. sensitizer to insoluble polythioether-containing materials. Additionally, on following the photocure, the cured polythioether can be heated preferably in the range 50°-250° C to imidize the amide-acid thereby improving the high temperature properties of the cured material.

Further, in accord with the instant invention, there are provided methods of preparing an amide-acid polyene which comprises reacting in substantially stoichiometric amounts (1) at least one primary diamine having the structural formula: $H_2N-R-NH_2$ wherein R is a divalent organic moiety containing at least 2 carbon atoms, the two amino groups of said diamine each attached to separate carbon atoms of said divalent organic moiety with (2) at least one anhydride-containing member of the group consisting of

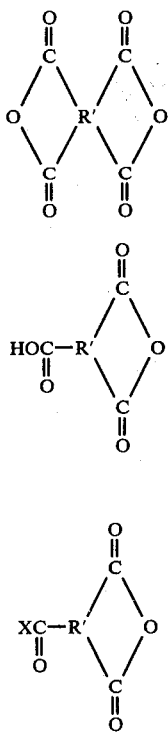

wherein R' is an aromatic residue attached to at least 3 carboxyl groups at least two of which groups are attached to adjacent carbon atoms on the aromatic residue and X is a halide radical and (3) an ethylenically unsaturated alcohol of the formula: $HO{-}(A){-}(Y)_m$ wherein A is an alkylene group having from 1 to 10 carbon atoms;

Y is a member of the group consisting of $-CR''{=}CH_2$ $-O-(CH_2)_d-CR''{=}CH_2$ and

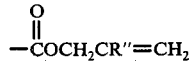

R" is hydrogen or methyl; and m and d are 1 to 10. If desired, when using a dianhydride, a polyamide acid structure containing up to 10 repeating units can be obtained by reacting sufficient diamine with the dianhydride prior to reacting the thus formed polymer with the ethylenically unsaturated alcohol.

The procedure for forming the amide-acid from the primary diamine and the anhydride-containing member is well known and conventional. That is, the amide-acid is prepared by mixing at least one primary diamine with at least one anhydride-containing member preferably in an inert organic solvent for at least the product and preferably one reactant under essentially anhydrous conditions for a time preferably of at least 2 minutes and at a temperature not higher than 180° C to provide at least 70% of the corresponding amide-acid. It should be understood that it is not necessary that the resultant product be totally amide-acid and that it is desirable that the product contain not more than 30% weight of imide, the remainder being the amide-acid. Thus, while the aforementioned conventional process for preparing amide-acid should be conducted preferably below 50° C to provide substantially 100% by weight of the amide-acids, higher temperatures will still provide a product containing substantial amounts of the amide-acid.

In practicing the instant invention all synthesis reactions are carried out under substantially anhydrous conditions in the presence of an inert gas (e. g. nitrogen, argon or helium) blanket. Additionally, all the synthesis reactions are preferably carried out in the presence of a solvent. The solvents useful for synthesizing the polyenes of the instant invention are organic solvents which do not chemically react with either of the reactants (the diamines or the dianhydrides) or the final amide-acid product. Additionally, besides being inert to the reaction system and being a solvent for the product, the organic solvent should be a solvent for at least one of the reactants and, preferably, for both of the reactants. The normally liquid organic solvents of the N,N-dialkylcarboxylamide class are useful as solvents in the process of the instant invention. Preferred solvents are low molecular weight members of this class, particularly N,N-dimethylformamide and N,N-dimethylacetamide. The solvents are readily removed from the amide-acid by evaporation, displacement or diffusion. Other useful solvents include, but are not limited to, N,N-diethylformamide; N,N-diethylacetamide; N,N-dimethylmethoxyacetamide; N-methyl captolactam; dimethylsulfoxide; N-methyl-2-pyrrolidone; tetramethylene urea; pyridine; dimethylsulfone; hexamethylphosphormide; tetramethylenesulfone; formamide; N-methylformamide; N-acetal-2-pyrrolidone; and the like. The solvents can be used alone, in a combination of the aforesaid solvents or in combination with poorer solvents such as toluene benzonitrile, dioxane, butyrolactone, xylene, chlorobenzene and cyclohexane.

More specifically, the reaction conditions for forming the various polyenes depending on which anhydride-containing member is employed are as follows.

To form the dianhydride amide-acid from a dianhydride and a diamine, each reactant is put into solution prior to mixing together. The admixture during reaction is maintained at a temperature in the range from 25° up to preferably below 100° C. Preferably, the diamine is added to the dianhydride but the reaction is operable if the sequence is reversed. In either sequence, the reactants are added to each other slowly to restrict the formation of very high molecular weight polymers. The mole ratio of the dianhydride to the diamine is 2:1 for monomeric amide-acids. A mole ratio of 1:1 can be employed should polyamide-acid be desired. Any mole ratio between these ratios is operational. The amide-acid polyene is formed by adding an unsaturated alcohol which can be, but need not be, in solution prior to its addition. The reaction is carried out at temperatures between room temperature and below 100° C, preferably 60°-80° C for periods ranging from 2 minutes to 3 hours. The resultant product is worked up by repeatedly washing the reaction mixture with a large excess of water while vigourously agitating the admixture. The water layer is discarded and the resulting viscous gum is then dried by dissolving it in an alcohol/benzene azeotropic mixture and azeotroping off the water. The azeotropic solvent used alone or as a mixture of solvents can be of any kind as long as it dissolves the gum and has an azeotropic boiling point below about 100° C.

To form a dicarboxylic amide-acid from a diamine and an acid anhydride, the reaction can be carried out in the presence or absence of the aforementioned solvent. If no solvent is used, the reactants are mixed in the flask and the flask is heated until the reactants react vigorously at a temperature ranging from 25° C up to 180° C, preferably 150°–175° C. If a solvent is employed, the diamine solution is preferably added to the anhydride but a reverse of the sequence is operable. The temperature range of the reaction when a solvent is employed is usually between 25° C to 100° C. The dicarboxylic acid amide-acid solution is vigorously washed with water and the resulting viscous gum is then dried by dissolving it into an alcohol/benzene azeotropic mixture and azeotroping off the water. To form the amide-acid polyene from this amide-acid, a conventional esterification reaction is performed. The unsaturated alcohol can act as a solvent per se or additional solvents such as benzene, toluene, isopropyl alcohol/benzene can be employed. A catalyst such as those well known in the esterification art, e. g. p-toluene sulfonic acid, methane sulfonic acid, sulfuric acid, phosphoric acid, hydrochloric acid, $BF_3$-etherate, camphor sulfonic acid and the like, may be employed. The solvent and/or unreacted alcohol is stripped off to recover the amide-acid polyene product.

When the anhydride-containing member is an anhydride acid halide, it is preferable to form the ester anhydride from the reaction of the anhydride acid halide and the unsaturated alcohol prior to reaction with the diamine. The ester anhydride is formed by putting both reactants, i. e. the anhydride acid halide and the unsaturated alcohol in solution prior to admixing same. The reactants are added in a mole ratio of approximately 1:1. The unsaturated alcohol is added slowly to the anhydride acid halide while the reaction solution is sparged vigorously with a dry inert gas (e. g. nitrogen, argon or helium) to remove the hydrogen halide. The reaction is carried out at slightly below, preferably 10° C below, refluxing temperature. After the addition of all the alcohol is complete, the reaction is continued until all the hydrogen halide has been removed. The diamine, in a solvent, is added to the ester anhydride (at a diamine to anhydride ratio of 2:1) while maintaining the reaction mixture in a range between 25° C to about 100° C, preferably between 50° and 70° C, until the IR absorption bands of the anhydride carbonyl groups disappear. The amide-acid polyene product is recovered by distilling off the solvent at low pressure using a temperature of preferably not greater than 100° C.

The diamines operable in the instant invention are primary diamines having the structural formula $H_2N$—R—$NH_2$ wherein R is a divalent organic moiety derived from or containing an aromatic, aliphatic, cycloaliphatic, heterocyclic or a combination of aromatic and aliphatic groups containing at least 2 carbon atoms, the 2 amino groups of said diamine are each attached to separate carbon atoms of said divalent organic moiety. Diamines which are operable in the instant invention include, but are not limited to, 4,4'-diamino-diphenyl methane; benzidine; 3,3'-dichlorobenzidine; 4,4'-diamino-diphenyl sulfide; 3,3'-diamino-diphenyl sulfone; 4,4'-diamino-diphenyl sulfone; 4,4'-diamino-diphenyl ether; 1,5-diamino naphthalene; meta-phenylenediamine; 4,4'-diamino-diphenyl propane. para-phenylenediamine; 3,3'-dimethyl-4,4'-biphenyl diamine; 3,3'-dimethoxy benzidine; 2,4-bis(beta-amino-t-butyl)toluene; bis-(para-beta-amino-t-butyl-phenyl) ether; bis-(para-beta-methyl-delta-amino-pentyl)benzene; bis-para-(1,1-dimethyl-5-amino-pentyl)benzene; 1-isopropyl-2,4-metaphenylene diamine; m-xylylene diamine; p-xylylene diamine; di(para-amino-cyclohexyl)methane; hexamethylene diamine; hepta-methylene diamine; octamethylene diamine, nonamethylene diamine, decamethylene diamine; 3-aminomethyl-3,5,5-trimethylcyclohexyl amine; 3-methylheptamethylene diamine; 4,4-dimethylheptamethylene diamine; 2,11-diaminododecane; 1,2-bis-(3-aminopropoxy ethane); 2,2-dimethyl propylene diamine; 3-methoxy-hexamethylene diamine; 2,5-dimethylhexamethylene diamine; 2,5-dimethylheptamethylenediamine; 3-methylheptamethylene diamine; 5-methylnonamethylenediamine; 2,17-diamino-eicosadecane; 1,4-diamino-cyclohexane; 1,10-diamino-1,10-dimethyldecane; 1,12-diamino-octadecane; 2,4 toluene diamine; 2,6 toluene diamine; 1,3-bis(aminomethyl)cyclohexane; N,N'-bis (3-aminopropyl) dimethyl hydantoin; $H_2N$ $H_2N(CH_2)_3O(CH_2)_2O(CH_2)_3NH_2$; $H_2N(CH_2)_3S(CH_2)_3NH_2$; $H_2N(CH_2)_3N(CH_3)(CH_2)_3NH_2$ and mixtures thereof.

The anhydride-containing member useful for forming polyenes in the instant invention is a member of the group consisting of:

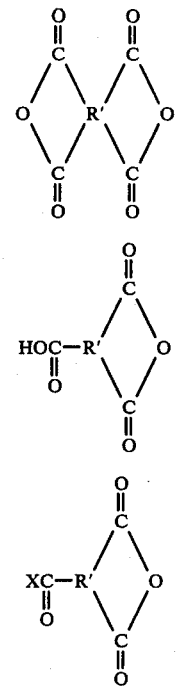

wherein R' is an aromatic residue attached to at least 3 carboxyl groups at least two of which groups are attached to adjacent carbon atoms on the aromatic residue and X is a halide radical. Anhydride-containing members operable in the instant invention to form amide-acid polyenes include, but are not limited to, pyromellitic dianhydride; 2,3,6,7-naphthalene tetracarboxylic dianhydride; 3,3',4,4'-diphenyl tetracarboxylic dianhydride; 1,2,5,6-naphthalene tetracarboxylic dianhydride; 2,2',3,3'-diphenyl tetracarboxylic dianhydride; 2,2-bis(3,4-dicarboxyphenyl) propane dianhydride; bis(3,4-dicarboxyphenyl)sulfone dianhydride; perylene 3,4,9,10-tetracarboxylic acid dianhydride; bis(3,4-dicarboxyphenyl)ether dianhydride; bis (3,4-dicarboxyphenyl) sulfone dianhydride, ethylene tetracarboxylic acid dianhydride; trimellitic anhydride acid halide, e. g. trimellitic anhydride acid chloride benzophenonetetracarboxylic anhydride; trimellitic anhydride and the like.

Ethylenically unsaturated alcohols suitable for use in the instant invention to form amide-acid polyenes are those of the formula: HO—(A)—(Y)$_m$ wherein A is an alkylene group having from 1 to 10 carbon atoms;

Y is a member of the group consisting of $-CR''=CH_2$, $-O-(CH_2)_d-CR''=CH_2$ and

R'' is hydrogen or methyl; and $m$ and $d$ and 1 to 10.

Illustrative of the operable reactive unsaturated alcohols which react with the amide-acid to give the desired polyene include, but are not limited to, allyl and methallyl alcohol, crotyl alcohol, ω-undecylenyl alcohol, 2-vinyloxyethanol, vinylhydroxyethyl sulfide, propargyl alcohol, hydroxy ethyl acrylate, hydroxy ethyl methacrylate, 1-allylcyclopentanol, 2-methyl-3-butene-2-ol, diallyl malate, hydroxy propyl acrylate, hydroxy propyl methacrylate. Reactive unsaturated derivatives of polyhydric alcohols such as glycols, triols, tetraols, etc., are also suitable. Representative examples include trimethylolpropane- or trimethylolethane diallyl ethers, pentaerythritol triallyl ether and the like. Mixtures of various reactive unsaturated alcohols are operable as well. Additionally, a suitable ethylenically unsaturated alcohol can be prepared by reacting one mole of a polyvinyl alcohol containing 10 hydroxyl groups with 9 moles of allylchloride to obtain an alcohol having 9 ethylenically unsaturated sites.

The amide-acid polyenes of the instant invention can be imidized per se by heating the polyene in the range 50°–250° C. Heating periods at the low end of the temperature range are necessarily of longer duration than those at the high end of the range to affect imidization.

The polyenes of the instant invention can also be imidized and cured in combination with a polythiol in the presence of a free radical generating agent. In some instances the polyene/polythiol composition is cured by adding a photosensitizer to the composition and exposing it to U.V. radiation followed by heating to effect imidization. In other instances the same formulation is heated first to cause imidization and, thereafter, subjected to U.V. radiation to effect curing. Additionally, both imidization and curing can be effected in one step by adding a chemical free radical generating agent, e. g. benzpinacol to the polyene/polythiol composition, and, thereafter, heating to effect both imidization and curing. Additionally, the polyene per se can be imidized by heating and, thereafter, admixed with a polythiol and photosensitizer for U.V. curing. These methods will be shown in the examples hereinafter.

Polythiol as used herein refers to simple or complex organic compounds having a multiplicity of pendant or terminally positioned —SH functional groups per average molecule.

On the average the polythiol must contain 2 or more —SH groups/molecule and have a viscosity range of essentially 0 to 20 million centipoises (cps) at 70° as measured by a Brookfield Viscometer either alone or when in the presence of an inert solvent, aqueous dispersion or plasticizer. Operable polythiols in the instant invention usually have molecular weights in the range about 94 to about 20,000, and preferably from about 100 to about 10,000.

The polythiols operable in the instant invention may be exemplified by the general formula $R_8-(SH)_n$ where $n$ is at least 2 and $R_8$ is a polyvalent organic moiety. Thus $R_8$ may contain cyclic groupings and hetero atoms such as N, P or O and primarily contains carbon-carbon, carbon-hydrogen, carbon-oxygen, or silicon-oxygen containing chain linkages.

One class of polythiols operable with polyenes to obtain essentially odorless polythioether products are esters of thiol-containing acids of the formula $HS-R_9-COOH$ where $R_9$ is an organic moiety with polyhydroxy compounds of structure $R_{10}-OH)_n$ where $R_{10}$ is an organic moiety and $n$ is 2 or greater. These components will react under suitable conditions to give a polythiol having the general structure:

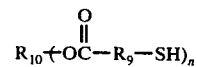

where $R_9$ and $R_{10}$ are organic moieties and $n$ is 2 or greater.

Certain polythiols such as the aliphatic monomeric polythiols (ethane dithiol, hexamethylene dithiol, decamethylene dithiol, tolylene-2,4-dithiol, etc. and some polymeric polythiols such as a thiol-terminated ethylcyclohexyl dimercaptan polymer, etc. and similar polythiols which are conveniently and ordinarily synthesized on a commercial basis, although having obnoxious odors, are operable in this invention but many of the end products are not widely accepted from a practical, commercial point of view. Examples of the polythiol compounds preferred for this invention because of their relatively low odor level include but are not limited to esters of thiogylcolic acid ($HS-CH_2COOH$), α-mercaptopropionic acid ($HS-CH(CH_3)-COOH$ and β-mercaptopropionic acid ($HS-CH_2CH_2COCH$) with polyhydroxy compounds such as glycols, triols, tetraols, pentaols, hexaols, etc. Specific examples of the preferred polythiols include but are not limited to ethylene glycol bis (thioglycolate), ethylene glycol bis (β-mercaptopropionate), trimethylolpropane tris (thioglycolate), trimethylolpropane tris (β-mercaptopropionate), pentaerythritol tetrakis (thioglycolate) and pentaerythritol tetrakis (β-mercaptopropionate), all of which are commercially available. A specific example of a preferred polymeric polythiol is polypropylene ether glycol bis (β-mercaptopropionate) which is prepared from polypropylene-ether glycol (e.g. Pluracol P2010, Wyandotte Chemical Corp.) and β-mercaptopropionic acid by esterification.

The preferred polythiol compounds are characterized by a low level of mercaptan-like odor initially, and after reaction, give essentially odorless polythioether end products which are commercially attractive and practically useful resins or elastomers for both indoor and outdoor applications.

Prior to curing, the photocurable polymer may be formulated for use as 100% solids, or disposed in organic solvents, or as solutions, dispersions or emulsions in aqueous media.

The photocurable polymer compositions prior to curing may readily be pumped, poured, siphoned, brushed, sprayed, doctored, or otherwise handled as desired. Following application, curing in place to a solid resin or elastomer may be effected either very rapidly or extremely slowly as desired by manipulation of the compounding ingredients and the method of curing.

To obtain the maximum strength, solvent resistance, creep resistance, heat resistance and freedom from tackiness, the reactive components consisting of the polyenes and polythiols are formulated in such a manner as to give solid, crosslinked, three dimensional network polythioether polymer systems on curing. In order to achieve such infinite network formation, the individual polyenes and polythiols must each have a functionality of at least 2 and the sum of the functionalities of the polyene and polythiol components must always be greater than 4. Blends and mixtures of various polyenes and various polythiols containing said functionality are also operable herein.

Functionality as used herein refers to the average number of ene or thiol groups per molecule in the polyene or polythiol, respectively. For example, a triene is a polyene with an average of three reactive carbon to carbon unsaturated groups per molecule, and thus a functionality (f) of three. A dithiol is a polythiol with an average of two thiol groups per molecule and thus has a functionality (f) of two.

The term reactive unsaturated carbon to carbon groups means groups which will react under proper conditions as set forth herein with thiol groups to yield the thioether linkage

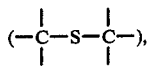

as contrasted to the term unreactive carbon to carbon unsaturation which means

groups found in aromatic nuclei (cyclic structures exemplified by benzene, pyridine, anthracene, and the like) which do not under the same conditions react with thiols to give thioether linkages. For purposes of brevity, this term will hereinafter be referred to generally as reactive unsaturation or a reactive unsaturated compound.

As used herein, the term polyvalent means having a valence of two or greater.

Prior to curing, the polyene and polythiol components are admixed in a suitable manner so as to form a homogeneous curable mixture. Thus, the polyene and polythiol reactants can be admixed without the necessity of using a solvent at room temperature or slightly elevated temperatures up to about 80° C or, if desired, the reactants may be dissolved in a suitable solvent and, thereafter, the solvent can be removed by suitable means such as evaporation.

The compositions to be cured in accord with the present invention may, if desired, include such additives as antioxidants, accelerators, dyes, inhibitors, activators, fillers, thickeners, pigments, anti-static agents, flame-retardant agents, surface-active agents, extending oils, plasticizers, thixotropic agents and the like within the scope of this invention. Such additives are usually pre-blended with the polyene or polythiol prior to or during the compounding step. The aforesaid additives may be present in quantities up to 500 or more parts based on 100 parts by weight of the polyene-polythiol curable compositions and preferably 0.005–300 parts on the same basis.

The polythioether-forming components and compositions, prior to curing, may be admixed with or blended with reactive diluents, other monomeric and polymeric materials such as thermoplastic resins, elastomers or thermosetting resin monomeric or polymeric compositions.

Non-limiting reactive diluents operable herein include ethylene glycol diacrylate, ethylene glycol dimethyacrylate, diethylene glycol diacrylate, diethylene glycol dimethacrylate, trimethylol propane triacrylate, trimethylol propane trimethacrylate, pentaerythritol tetracrylate, pentaerythritol tetramethacrylate, 1,6-hexanediol diacrylate, 1,6-hexanediol dimethacrylate, pentaerythritol triacrylate, neopentyl glycol diacrylate and mixtures thereof. The resulting blend may be subjected to conditions for curing or co-curing of the various components of the blend to give cured products having unusual physical properties.

Although the mechanism of the curing reaction is not completely understood, it appears most likely that the curing reaction may be initiated by most any free radical generating source which dissociates or abstracts a hydrogen atom from an SH group, or accomplishes the equivalent thereof. Generally, the rate of the curing reaction may be increased by increasing the temperature of the composition at the time of initiation of cure. In most applications, however, the curing is accomplished conveniently and economically by operating at ordinary room temperature conditions.

Operable curing initiators or accelerators include radiation such as actinic radiation, e.g., ultraviolet light, lasers; ionizing radiation such as gamma radiation, x-rays, corona discharge, etc.; as well as chemical free radical generating compounds such as azo, peroxidic, etc., compounds.

Azo or peroxidic compounds (with or without amine accelerators) which decompose at ambient conditions are operable as free radical generating agents capable of accelerating the curing reaction include benzoyl peroxide, di-t-butyl peroxide, cyclohexanone peroxide with dimethyl aniline or cobalt naphthenate as an accelerator; hydroperoxides such as hydrogen peroxide, cumene hydroperoxide, t-butyl hydroperoxides; peracid compounds such as t-butylperbenzoate, peracetic acid; persulfates, e.g., ammonium persulfate; azo compounds such as azobis-isobutyronitrile and the like.

These free radical generating agents are usually added in amounts ranging from about 0.001 to 10 percent by weight of the curable solid polyene-polythiol composition, preferably .01 to 5 percent.

Additionally, substituted or unsubstituted pinacols such as those set out in copending application having Ser. No. 651,365, assigned to the same assignee and incorporated by reference herein, are also operable as free radical generators to form imide-containing cured polythioethers. That is, the amide-acid polyene, polythiol and pinacol can be heated to form an imide-containing, solid, cured polythioether as will be shown in an example hereinafter.

The substituted or unsubstituted pinacols operable herein have the general formula:

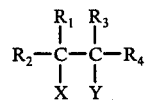

wherein $R_1$ and $R_3$ are the same or different substituted or unsubstituted aromatic radicals, $R_2$ and $R_4$ are substituted or unsubstituted aliphatic or aromatic radicals and X and Y which may be the same or different are hydroxyl, alkoxy or aryloxy.

Preferred pinacols are those wherein $R_1$, $R_2$, $R_3$, and $R_4$ are aromatic radicals, especially phenyl radical and X and Y are hydroxyl.

Examples of this class of compounds include but are not limited to benzopinacol, 4,4'-dichlorobenzopinacol, 4,4'-dibromobenzopinacol, 4,4'-diiodobenzopinacol, 4,4',4",4'''-tetrachlorobenzopinacol, 2,4-2',4'-tetrachlorobenzopinacol, 4,4'-dimethylbenzopinacol, 3,3'-dimethylbenzopinacol, 2,2'-dimethylbenzopinacol, 3,4-3',4'-tetramethylbenzopinacol, 4,4'-dimethoxybenzopinacol, 4,4',4",4'''-tetramethoxybenzopinacol, 4,4'-diphenylbenzopinacol, 4,4'-dichloro-4",4'''-dimethylbenzopinacol, 4,4'-dimethyl-4",4'''-diphenylbenzopinacol, xanthonpinacol, fluorenonepinacol, acetophenonepinacol, 4,4'-dimethylacetophenone-pinacol, 4,4'-dichloro-acetophenonepinacol, 1,1,2-triphenyl-propane-1,2-diol, 1,2,3,4-tetraphenylbutane-2,3-diol, 1,2-diphenylcyclobutane-1,2-diol, propiophenone-pinacol, 4,4'-dimethylpropiophenone-pinacol, 2,2'-ethyl-3,3'-dimethoxy-propiophenone-pinacol, 1,1,1,4,4,4-hexafluoro-2,3-diphenyl-butane-2,3-diol.

As further compounds according to the present invention, there may be mentioned: benzopinacol-mono methylether, benzopinacol-mono-phenylether, benzopinacol monoisopropyl ether, benzopinacol monoisobutyl ether, benzopinacol mono (diethoxy methyl) ether and the like.

The pinacol is added to the composition in amounts ranging from 0.01 – 5% preferably 0.1 – 3% by weight based on the weight of the ethylenically unsaturated compound and the polythiol.

The curing period may be retarded or accelerated from less than 1 minute to 30 days or more.

Conventional curing inhibitors or retarders which may be used in order to stabilize the components or curable compositions so as to prevent premature onset of curing may include hydroquinone; p-tert-butyl catechol; 2,6-di tert-butyl-p-methylphenol; phenothiazine; N-phenyl-2-naphthylamine; phosphorous acid; pyrogallol and the like.

The preferred free radical generator for the curing reaction is actinic radiation, suitably in the wavelength of about 2000 to 7500A, preferably for 2000 to 4000A.

A class of actinic light useful herein is ultraviolet light, and other forms of actinic radiation which are normally found in radiation emitted from the sun or from artificial sources such as Type RS Sunlamps, carbon arc lamps, xenon arc lamps, mercury vapor lamps, tungsten halide lamps and the like. Ultraviolet radiation may be used most efficiently if the photocurable polyene/polythiol composition contains a suitable photocuring rate accelerator. Curing periods may be adjusted to be very short and hence commerically economical by proper choice of ultraviolet source, photocuring rate accelerator and concentration thereof, temperature and molecular weight, and reactive group functionality of the polyene and polythiol. Curing periods of less than about 1 second duration are possible, especially in thin film applications such as desired, for example, in coatings, adhesives and photoimaged surfaces.

Various photosensitizers, i.e., photocuring rate accelerators are operable and well known to those skilled in the art. Examples of photosensitizers include, but are not limited to, benzophenone o-methoxybenzophenone, acetophenone, o-methoxyacetophenone, acenaphthene-guinone, methyl ethyl ketone, valerophenone, hexanophenone, δ-phenylbutyrophenone, p-morpholinopropiophenone, dibenzosuberone, 4-morpholinobenzophenone, benzoin, benzoin methyl ether, 4'-morpholinodeoxybenzoin, p-diacetylbenzene, 4-aminobenzophenone, 4'-methoxyacetophenone, benzaldehyde, o-methoxybenzaldehyde, α-tetralone, 9-acetylphenanthrene, 2-acetylphenanthrene, 10-thioxanthenone, 3-acetylphenanthrene, 3-acetylindole, 9-fluorenone, 1-indanone, 1,3,5-triacetylbenzene, thioxanthen-9-one, xanthene-9-one, 7-H-benz[de]anthracen-7-one, 1-naphthaldehyde, benzoin tetrahydropyranyl ether, 4,4'-bis (dimethylamino)benzophenone, fluorene-9-one, 1'-acetonaphthone, 2'-acetonaphthone, triphenylphosphine, tri-o-tolylphosphine, acetonaphthone and 2,3-butanedione, benz[a]anthracene 7,12 dione, 2,2-dimethoxy-2-phenylacetone, diethoxyacetophenone, dibutoxyacetophenone, etc., which serve to give greatly reduced exposure times and thereby, when used in conjunction with various forms of energetic radiation, yield very rapid, commercially practical time cycles by the practice of the instant invention.

These photocuring rate accelerators may range from about 0.005 to 50 percent by weight of the photocurable polyenepolythiol composition, preferably 0.05 to 25 percent.

The mole ratio of the ene/thiol groups for preparing the curable composition is from about 0.2/1.0 to about 8/1.0, and preferably from 0.5/1.0 to about 2/1.0 group ratio.

The curable amide-acid polyene or imide polyene and polythiol compositions are used in preparing solid, cured crosslinked insoluble polythioether polymeric products having many and varied uses, examples of which include, but are not limited to, coatings; adhesives; films; molded articles; imaged surfaces, e.g. photoresists; printing plates; e. g. offset, lithographic, letterpress, gravures, etc., silverless photographic materials and the like.

Since the cured materials formed from the polyenepolythiol composition posses various desirable properties such as resistance to severe chemical and physical environments and have good high temperature properties on imidization, they are particularly useful for preparing coatings.

A general method for preparing coatings, comprises coating the curable composition on a solid surface of a substrate such as plastic, rubber, glass, ceramic, metal, paper and the like; exposing directly to radiation, e.g., U.V. light until the curable composition cures and crosslinks in the exposed areas. The resulting products are cured coatings on suitable substrates or supports.

In forming the composition comprised of the polythiol and the polyene, it is desirable that the photocurable composition contain a photocuring rate accelerator from about 0.005 to 50 parts by weight based on 100 parts by weight of the aforementioned polyene and polythiol.

It is to be understood, however, that when energy sources, e.g., ionizing radiation, other than visible or ultraviolet light, are used to initiate the curing reaction, photocuring rate accelerators (i.e., photosensitizers, etc.) are not required in the formulation.

When U.V. radiation is used, an intensity of 0.0004 to 60.0 watts/cm$^2$ in the 250–400 nanometer region is usually employed.

The following examples will aid in explaining, but should not be deemed limiting, the instant invention. In all cases unless otherwise noted, all parts and percentages are by weight.

The termal shock and thermoplastic flow test were carried out in accord with the procedure set out in National Electric Manufacturers Association (NEMA) standards publication/No. MW 1000–1973.

In all examples herein the U.V. radiation from the Addelux lamp had a surface intensity of 13,400 microwatts/cm² and from the pulsed xenon lamp a surface intensity of 22,000 microwatts/cm².

EXAMPLE 1

To a 3-necked, 300 ml round bottom flask equipped with stirrer, addition funnel and reflux condenser was charged under a nitrogen blanket 40.62 g of pyromellitic dianhydride (PMAn) and 75 ml of freshly distilled N-methyl-2-pyrrolidone (NMP). To the addition funnel was added 22.11 g of N,N'-bis-(3-aminopropyl)dimethylhydantoin and 25 ml of NMP. The PMAn was first dissolved in the NMP and then, while the temperature was kept between 40°–60° C, the diamine was added slowly, dropwise, during a period of 1.5 hours. When the addition was completed, the temperature of the reaction mixture was raised to and kept at between 70°–80° C. while adding 38.71 g trimethylolpropane diallyl ether during a period of about 20 minutes. Some more NMP was added to the reaction mixture after addition of each reagent. Once the alcohol was added, the mixture was kept between 70°–80° C for one hour, after which time it was cooled and worked up as follows:

The very viscous reaction mixture was dropped into a large quantity of water and shaken vigorously. After discarding the water layer, vigorous agitation with water was repeated three more times. The viscous gum was then dissolved in methanol, and the solution was transferred into a round bottom flask, provided with stirring, Dean-Stark trap and a reflux condenser. 130 ml of benzene was then added and the solution was then boiled vigorously while distilling out most of the methanol along with most of the water. The remaining water, methanol and benzene were then distilled off under reduced pressure at a maximum temperature of 80° C. The brown very viscous product weighed 95 g. The IR spectra indicated that at least 75% of this product was of the formula:

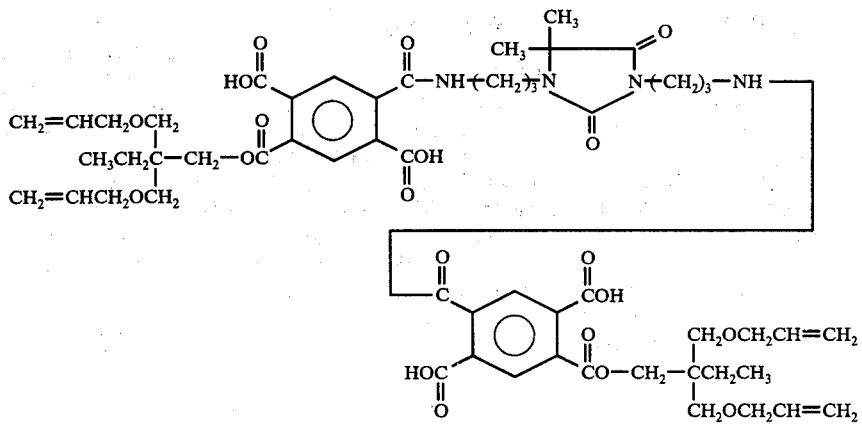

will hereinafter be referred to as Polyene A.

EXAMPLE 2

To a 3-necked, 300 ml round bottom flask equipped with stirrer and reflux condenser, was added under a nitrogen blanket 25.67 g. of 1,3-bis(aminomethyl)cyclohexane and 100 ml of dimethylformamide. The mixture was heated to approximately 125° C and while maintaining the temperature constant, 69.97 g. of trimellitic anhydride (TMAn) was added in three equal portions. The reaction was allowed to proceed for 1.5 hours and then was cooled to room temperature. The product was worked up by dropping the reaction mixture into a large volume of vigorously stirred water. The water layer was then discarded and the vigorous agitation of the gummy product with water was repeated. After discarding the water again, 25 ml of acetone was used to break up the gum while it started solidifying. To this slurry was added 500 ml of chloroform. The solid product was then filtered and reslurried in benzene. This slurry was then dried by azeotropic distillation, the white solid amide-acid was filtered and was then kept in a vacuum dissicator containing $P_2O_5$. To a 3-necked, 300 ml round bottom flask equipped with stirrer, reflux condenser and Dean-Stark trap, was added 5.0 g of the white solid amide-acid supra 50 ml of allyl alcohol and 0.1 g of concentrated $H_2SO_4$. The mixture was boiled and while allyl alcohol was distilled out of the flask in increments of about 10 ml, fresh allyl alcohol was added to the flask to replace the removed alcohol. This procedure was continued for several hours until sufficient esterification had occurred. Solids in the reaction mixture were then filtered off and the allyl alcohol in the filtrate was stripped under vacuum. The product was a light brown, very viscous liquid of the formula:

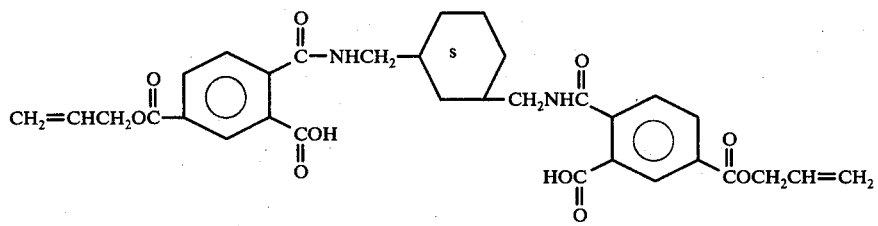

which will be referred to hereinafter as Polyene B.

EXAMPLE 3

To a 3-necked, 300 ml round bottom flask equipped with stirrer, reflux condenser and a modified Dean-Stark trap, was added under a nitrogen blanket 10.31 g. of trimelletic anhydride (TMAn) and 6.37 g. of N,N'-bis(3-aminopropyl)dimethylhydantoin. While the mixture was purged through with nitrogen, it was heated to about 160°-180° C. Soon after the fairly fast reaction occurred, the reaction product was cooled to about 80° C. 50 ml of allyl alcohol, 0.009 g. of hydroquinone and 0.224 g. of concentrated $H_2SO_4$ was then added to the pot and the Dean-Stark trap was filled with alumina so that the alcohol could be recirculated to the reaction flask while being dried by the alumina. The reaction mixture was refluxed for about one hour. Upon completion of the reaction, the excess allyl alcohol was stripped off under vacuum. The final product of the formula:

thylhydantoin. While the mixture was purged through with nitrogen, it was heated to about 160°-180° C. Soon after the fairly fast reaction occurred, the reaction product was cooled to about 80° C. 43.0 g. of allyl alcohol, and 5.56 g. of trimethylolpropane diallyl ether, 0.0009 g. of hydroquinone and 0.224 g. of concentrated $H_2SO_4$ was then added to the pot and the Dean-Stark trap was filled with alumina so that the alcohol could be recirculated to the reaction flask while being dried by the alumina. The reaction mixture was refluxed for about one hour. Upon completion of the reaction, the excess allyl alcohol was stripped off under vacuum. The final product of the formula:

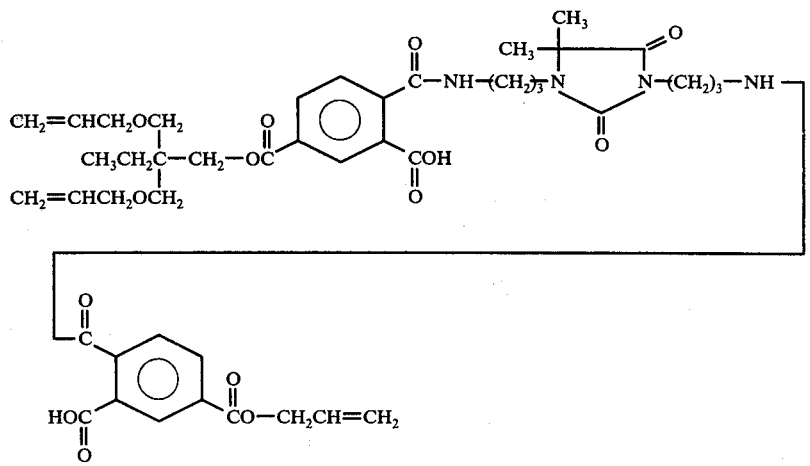

was a yellow-brown viscous material and will be referred to hereinafter as Polyene D.

EXAMPLE 5

To a 3-neck, 5-liter, round bottomed flask equipped with stirrer, addition funnel, thermometer, reflux condenser and a nitrogen sparge tube (gas disperse system)

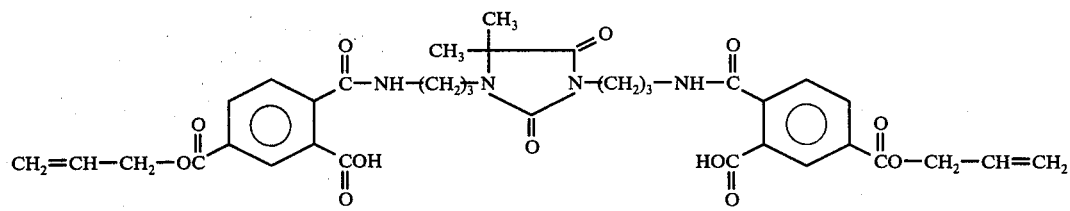

was a yellow-brown viscous material and will be referred to hereinafter as Polyene C.

EXAMPLE 4

To a 3-necked, 300 ml round bottom flask equipped with stirrer, reflux condenser and a modified Dean-Stark trap, was added under a nitrogen blanket 10.31 g. of TMAn and 6.37 g. of N,N'-bis(3-aminopropyl)dimewas added under nitrogen 322.4 g. of trimellitic anhydride acid chloride (TMAn. Cl) and 791 g. benzene. The mixture was heated until all the TMAn. Cl dissolved in the benzene. To this solution was added very slowly (via a dropping funnel) a 43% solution of trimethylolpropane diallyl ether in benzene (311.70 g. in 413 g. benzene) while the temperature of the contents in the reaction flask was kept just below 80° C with continuous N$_2$-sparging into the reaction solution. Once all the trimethylolpropane diallyl ether was added, the N$_2$-sparge was continued to remove all the HCl in the reaction mixture. 650 g. of benzene was then distilled out of the reaction vessel. The temperature of the reaction mixture was then lowered to about 60° C at which time a 49% solution of N,N'-bis (aminopropyl)dimethylhydantoin, in benzene (176.23 g. in 185 g. benzene) was added at a rate sufficient to sustain a temperature of about 55°-70° C. Once all the N,N'-bis (aminopropyl)-dimethylhydantoin was added, the reaction mixture was kept at 60° C until the IR absorption bands of the anhydride carbonyl groups disappeared. Analysis for unreacted amine groups showed that the amine content was less than 0.2 meq/g. The resultant product was obtained by distilling off the benzene under vacuum. The product (741 g) contained 24% by weight imide and an amideacid polyene of the formula:

aminomethyl-3,5,5-trimethylcyclohexylamine and 25 ml of NMP. The PMAn was first dissolved in the NMP and then, while the temperature was kept between 40°-60° C, the diamine was added slowly, dropwise, during a period of 2.0 hours. When the addition was completed, the temperature of the reaction mixture was raised to and kept at between 70°-80° C while adding 41.41 g. of trimethylolpropane diallyl ether mixed with 9 ml of NMP during a period of about 5 minutes. Some more NMP was added to the reaction mixture after addition of each reagent. Once the alcohol was added, the mixture was kept between 70°-80° C for one hour, after which time it was cooled and worked up as follows:

The very viscous reaction mixture was dropped into a large quantity of water and shaken vigorously. After discarding the water layer, vigorous agitation with water was repeated three more times. The viscous gum was then dissolved in methanol, and the solution was

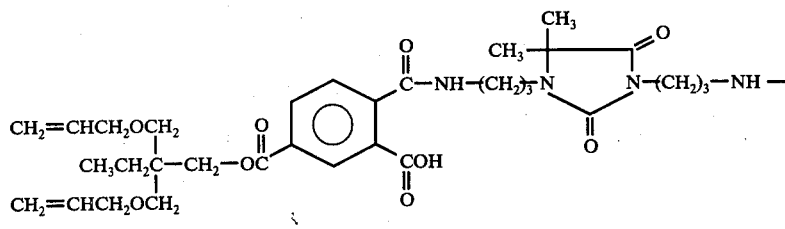

which will be referred to hereinafter as Polyene E.

EXAMPLE 6

To a 3-necked, 300 ml round bottom flask equipped with stirrer, addition funnel and reflux condenser was charged under a nitrogen blanket 43.44 g. of pyromellitic dianhydride (PMAn) and 75 ml of freshly distilled N-methyl-2-pyrrolidone (NMP). To the addition funnel was added 16.50 g. of isophorone diamine, i. e. 3- transferred into a round bottom flask, provided with stirring, Dean-Stark trap and a reflux condenser. 130 ml of benzene was then added and the solution was then boiled vigorously while distilling out most of the methanol, which carries out most of the water. The remaining water, methanol and benzene were then distilled off under reduced pressure at a maximum temperature of 80° C. The brown very viscous product wt. about 95 g of the formula:

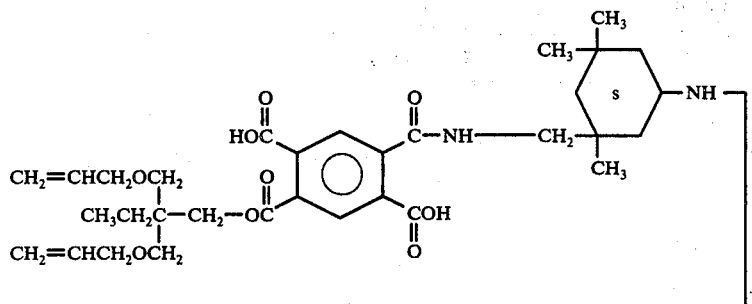

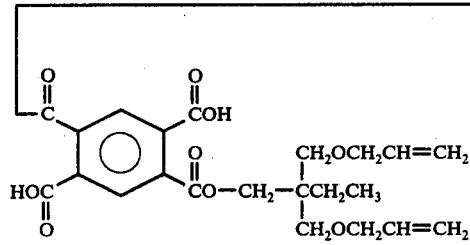

will hereinafter be referred to as Polyene F.

EXAMPLE 7

To a 4-necked, 1 l. round bottom flask equipped with stirrer, addition funnel, thermometer, Dean-Stark trap, and reflux condenser was charged under a nitrogen blanket 16.0 g of N,N'-bis(2-carboxyethyl)-dimethylhydantoin, 1.30 g of p-toluene sulfonic acid as catalyst and 100 ml of benzene. The mixture was refluxed until the Dean-Stark trap was full of benzene, and then 3.50 g of allyl alcohol and 12.91 g of trimethylolpropane diallyl ether in 50 ml of benzene was added during a period of 35 minutes. When no more water was azeotroping into the Dean-Stark trap, the heat was turned off and the product was worked up by washing it twice with 150 ml of water, then twice with 100 ml of 5% aq. NaHCO$_3$, and then again twice with 100 ml of water. The benzene layer containing the product was then dried with anhydrous MgSO$_4$, treated with decolorizing carbon, and then distilled under vacuum until all the benzene was taken off. The product, i. e.,

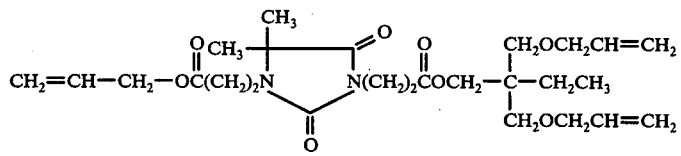

had a C≡C content of 5.80 mmoles/g and will be referred to hereinafter as Polyene G.

The polyenes of the instant invention can be imidized per se as is shown in the following examples.

EXAMPLE 8

A thin film of Polyene A from Example 1 was placed on a sodium chloride IR window and heated for 5 minutes at 210° C. The IR spectrum after heating said polyene showed the disappearance of the amide band and a significant increase of the imide band evidencing imidization. The imidized polyene of the formula:

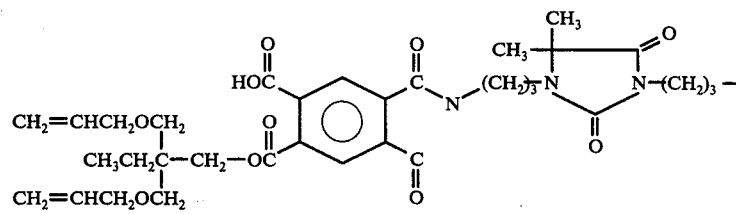

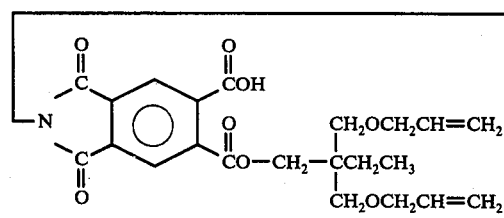

will hereinafter be referred to as imidized Polyene H.

EXAMPLE 9

Example 8 was repeated except that Polyene E from Example 5 was substituted for Polyene A. The results were the same. The imidized polyene of the formula:

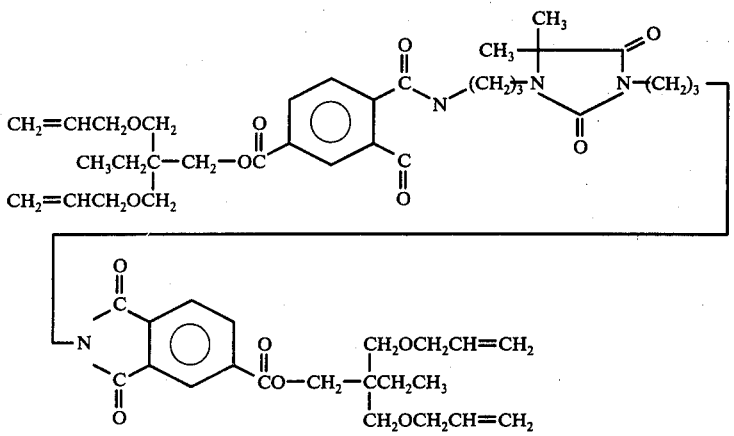

will hereinafter be referred to as imidized Polyene J.

Example 8 was repeated using Polyenes B, C, D and F from Examples 2, 3, 4 and 6. The IR spectrum after heating said polyenes in each case showed the disappearance of the imide band and a significant increase of the imide band.

The following examples show various curable compositions of either the amide-acid polyene or imide polyene in combination with a polythiol and methods of curing to obtain a cured polythioether product.

EXAMPLE 10

5.0 g of Polyene E from Example 5 was admixed with 1.57 g of the bis(3-mercaptopropionate) of 1,3-bis (2-hydroxyethyl)-5,5-dimethylhydantoin, 0.20 g of pentaerythritol tetrakis ($\beta$-mercaptopropionate), 0.10 g of trimethylolpropane tris($\beta$-mercaptopropionate) and 0.137 g of 2,2-dimethoxy-2-phenylacetophenone until homogeneous. The admixture was exposed to U.V. radiation for 15 seconds from Addalux lamp to form a cured polythioether and, thereafter, heated for 5 minutes at about 210° C to imidize the polyene portion. The IR spectrum of the resultant cured solid product showed disappearance of the thiol and amide absorption bands and appearance of the imide absorption bands.

EXAMPLE 11

9.857 g of Polyene E from Example 5 was heated at 210° C for 5 minutes to imidize the polyene. The thus imidized polyene was admixed with 4.14 g of the bis (3-mercaptopropionate) of 1,3-bis(2-hydroxyethyl)-5,5-dimethylhydantoin, 0.40 g of pentaerythritol tetrakis ($\beta$-mercaptopropionate), 0.20 g of trimethylolpropane tris($\beta$-mercaptopropionate) and 0.147 g of benzoin isopropyl ether. The admixture was exposed to U.V. radiation from an Addalux lamp for 15 seconds. A cured polythioether product resulted.

EXAMPLE 12

Using the formulation of Example 10, the procedure was reversed and the formulation was heated for 5 minutes at 210° C followed by U.V. curing for 15 seconds under an Addalux lamp. A cured imidized polythioether product resulted.

EXAMPLE 13

10 g. of Polyene E from Example 5 was admixed with 4.6 g. of di(2-hydroxyethyl)dimethylhydantoin bis(3-mercaptopropionate), 2.5 g. of pentaerythritol tetrakis($\beta$-mercaptopropionate) and 0.166 g. of benzopinacol until homgeneous. The admixture was heated at 180° C for 5 minutes. A cured solid imidized polythioether product resulted.

The following examples show the utility of the polyene of the instant invention with a polythiol in forming an imidized cured polythioether coating when subjected to U.V. radiation and heat. When U.V. radiation is used, a photosensitizer or photocuring rate accelerator is usually added to the system along with various conventional stabilizers to extend shelf life.

The amide-acid polyenes combined with a polythiol will be compared with polyene/polythiol systems in which the polyene is not imidizable or is not imidized and thus does not have the improved higher temperature properties such as are desired in wire coating.

EXAMPLE 14

The following formulations were made up from accurately weighed ingredients and admixed until homogeneous:

| Formulation A | |
|---|---|
| 5.00 g. | Polyene A from Example 1 |
| 3.26 g. | tris(hydroxyethyl)isocyanurate tris (3-mercaptopropionate) |
| 0.083 g. | benzoin isopropyl ether (photosensitizer) |
| 0.826 g. | trimethylolpropane diallyl ether |
| 0.826 g. | dimercaptopropionate of N,N'-bis(2-hydroxyethyl) dimethylhydantoin |
| 0.083 g. | benzopinacol |
| 0.005 g. | stabilizer package |

| Formulation B | |
|---|---|
| 3.78 g. | Polyene A from Example 1 |
| 1.22 g. | tris(hydroxyethyl)isocyanurate tris (3-mercaptopropionate) |
| 0.50 g. | dimercaptopropionate of N,N'-bis(2-hydroxyethyl)dimethylhydantoin |
| 0.25 g. | trimethylolpropane diallyl ether |
| 0.10 g. | benzoin isopropyl ether |
| 0.005 g. | stabilizer package |

| Formulation C | |
|---|---|
| 5.00 g. | Polyene D from Example 4 |

-continued

Formulation C

| | |
|---|---|
| 4.28 g. | tris(hydroxyethyl)isocyanurate tris (3-mercaptopropionate) |
| 1.41 g. | dimercaptopropionate of N,N'-bis(2-hydroxyethyl)dimethylhydantoin |
| 0.36 g. | trimethylolpropane diallyl ether |
| 0.186 g. | benzoin isopropyl ether |
| 0.010 g. | stabilizer package |

Formulation D

| | |
|---|---|
| 10.0 g. | Polyene A from Example 1 |
| 3.25 g. | tris(hydroxyethyl)isocyanurate tris(3-mercaptopropionate) |
| 0.66 g. | dimercaptopropionate of N,N'-bis(2-hydroxyethyl) dimethylhydantoin |
| 0.28 g. | benzoin isopropyl ether |
| 0.014 g. | stabilizer package |

Formulation E

| | |
|---|---|
| 10.0 g. | Polyene F from Example 6 |
| 3.02 g. | dimethylolpropionic acid bis(3-mercaptopropionate) |
| 0.33 g. | benzoin isopropyl ether |
| 0.018 g. | stabilizer package |

Formulation F

| | |
|---|---|
| 5.0 g. | Polyene E from Example 5 |
| 2.07 g | dimercaptopropionate of N,N'-bis(2-hydroxyethyl)dimethylhydantoin |
| 0.20 g | commercially available pentaerythritol tetrakis (β-mercaptopropionate) |
| 0.10 g | trimethylolpropane tris(β-mercaptopropionate) |
| 0.137 g | 2,2-dimethoxy-2-phenylacetophenone |
| 0.009 g | stabilizer package |

Formulation G

| | |
|---|---|
| 45.0 g | diallyl maleate |
| 82.7 g | tris(hydroxyethyl)isocyanurate tris(3-mercaptopropionate) |
| 3.83 g | benzoin isopropyl ether |
| 1.99 g | stabilizer package |

Formulation H

| | |
|---|---|
| 20.00 g | Polyene G from Example 7 |
| 2.38 g | commercially available iso-diallylphthalate |
| 23.66 g | tris(hydroxyethyl)isocyanurate tris(3-mercaptopropionate) |
| 1.38 g | benzoin isopropyl ether |
| 1.41 g | stabilizer package |

EXAMPLE 15

A 24 AWG copper wire was passed through a degreasing bath of methylene chloride followed by drying. The wire was cut into 9 sections and each wire section was cooled with one of the Formulations A-H from Example 14 with the extra wire section also being coated with Formulation F, all at ambient conditions.

Each section of the thus coated wire was then passed through a die to insure a homogeneous thickness of 1 mil and through a surrounding bank of U.V. pulsed xenon lamps whose major spectral lines were all above 300 Angstroms at a speed of 20 feet per second for an exposure period of 2 seconds. The sunlamps were so positioned that the surface intensity on the radiation curable composition was 22,000 microwatts/cm². All the resulting wire sections had a smooth, cured coating of 1 mil thickness and showed good flexibility and adhesion on bending. The thus cured coated wire sections coated with Formulations A, B, C, D and one section coated with Formulation F were then heated at 210°-220° C for 5 minutes to affect imidization. All the wire sections with their cured coating were then subjected to standard NEMA heat shock and thermoplastic flow test. The results are shown in TABLE I.

TABLE I

Properties of Wire-Coated Formulations

| Formulation | Average Cut-Through Temperature (° C) | Heat Shock 20% Stretched Wire at 175° C for 30 Minutes |
|---|---|---|
| A | 220° | passed 1 × mandrel |
| B | 260° C | passed 3 × mandrel |
| C | — | passed 2 × mandrel |
| D | 210° | passed 2 × mandrel |
| E | 200° | passed 1 × mandrel |
| F (imidized) | 225° | passed 3 × mandrel |
| F (not imidized) | 125° | passed 2 × mandrel |
| G | 255° | failed 5 × mandrel |
| H | 100° | failed 5 × mandrel |

Thus, as can be seen from the data in TABLE I, the radiation curable formulations containing an imidized polyene (Formulations A-F) have improved high temperatures properties over conventional radiation curable polyene/polythiol formulations (Formulations G and H) wherein the polyene is not imidizable and over Formulation F which was not imidized.

The amide-acid polyenes of the instant invention can also be synthesized in polymeric form as shown by the following example:

EXAMPLE 16

To a 3-necked, 300 ml round bottom flask equipped with stirrer, addition funnel, thermometer and nitrogen sparge tube was charged under a nitrogen blanket 24.37 g. of pyromellitic dianhydride (PMAn) and 44 ml of freshly distilled N-methyl-2-pyrrolidone (NMP). The flask was heated to about 90° C to dissolve the PMAn, 13.4 g. of N,N'-bis(3-aminopropyl)dimethylhydantoin and 15 ml NMP were charged to the addition funnel. The flask was cooled to 75° C and the contents of the addition funnel were added to the flask over a one minute period. The contents of the flask was stirred at 70° C for 30 minutes after which 6.29 g. of allyl alcohol were added to the flask. The contents of the flask was then charged into chloroform and filtered. A light brown polymeric polyene product (molecular weight 6600 indicating 6-7 repeating units) resulted. The IR spectrum showed little or no imide present in the product and a substantial amide band present.

This polymeric polyene will be referred to hereinafter as Polyene K.

5 g of Polyene K were heated for 10 minutes at 220° C. The resultant product was dark brown, indicative of imidization.

5 g of Polyene K were admixed with 1.96 g of dimethylolpropionic acid bis(3-mercaptopropionate) and 0.139 g. of 2,2-dimethoxy-2-phenylacetophenone. The admixture was exposed to U.V. radiation for 3½ minutes from an Addulux lamp. A cured, solid polythioether resulted.

EXAMPLE 17

The formulation of Example 10 was coated to 1 mil thickness on each of the following substrates: paper, cardboard, aluminum foil, steel plate stock, "Myler"

polyester film, plywood, ceramic and a concrete block of the type used in building construction. The thus coated substrates were exposed to U.V. radiation for 30 seconds from an Addelux lamp to form a cured polythioether coating and, thereafter, heated for 5 minutes at 210° C to imidize the polyene portion.

What is claimed is:

1. An amide-acid polyene of the formula:

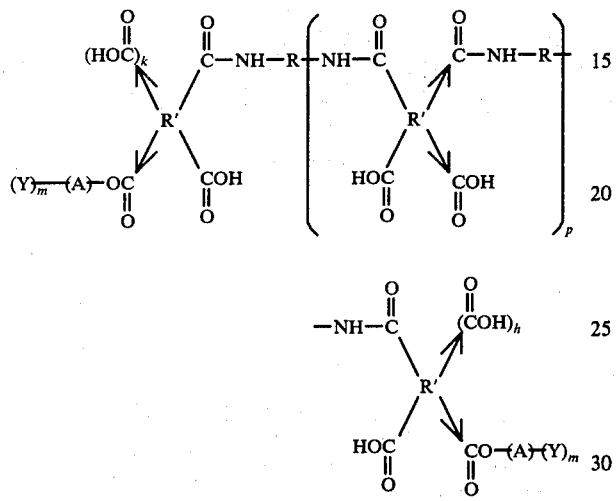

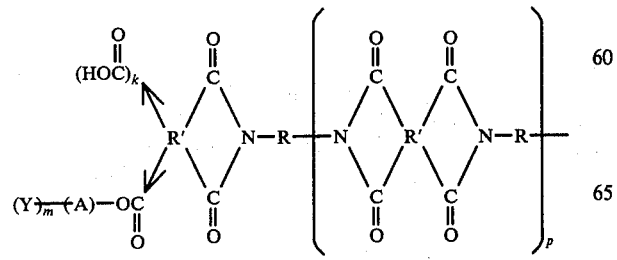

wherein → denotes isomerism, R is a divalent organic moiety remaining after a primary diamine has reacted to form amide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of —CR″=CH$_2$, —O—(CH$_2$)$_d$—CR″=CH$_2$ and

R″ is hydrogen or methyl; $k$ and $h$ are 0 or 1; $m$ and $d$ are 1 to 10 and $p$ is 0 to 10.

2. An imide-containing polyene of the formula

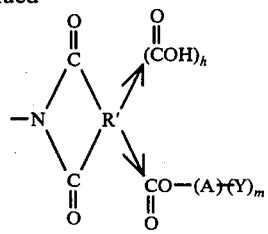

wherein → denotes isomerism, R is a divalent organic moiety remaining after a secondary diamide has reacted with adjacent carboxylic acid groups to form imide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of —CR″=CH$_2$, —O—(CH$_2$)$_d$—CR″=CH$_2$ and

R″ is hydrogen or methyl; $k$ and $h$ are 0 or 1; $m$ and $d$ are 1 to 10 and $p$ is 0 to 10.

3. A method of preparing an amide-acid polyene which comprises reacting in an inert atmosphere under anhydrous conditions in substantially stoichiometric amounts (1) at least one primary diamine having the structural formula: H$_2$N—R—NH$_2$ wherein R is a divalent organic moiety containing at least 2 carbon atoms, the two amino groups of said diamine each attached to separate carbon atoms of said divalent organic moiety with (2) at least one anhydride-containing member of the group consisting of

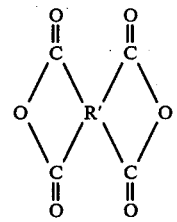

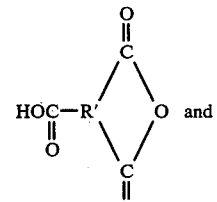

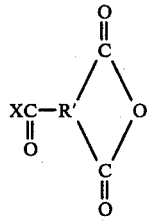

wherein R' is an aromatic residue attached to at least 3 carboxyl groups at least two of which groups are attached to adjacent carbon atoms on the aromatic residue and X is a halide radical and (3) an ethylenically unsaturated alcohol of the formula: HO—(A)—(Y)$_m$ wherein A is an alkylene group having from 1 to 10 carbon atoms;

Y is a member of the group consisting of —CR"=CH$_2$, —O—(CH$_2$)$_d$—CR"=CH$_2$ and

R" is hydrogen or methyl; and $m$ and $d$ are 1 to 10 at a temperature in the range 20° to 100° C in an organic solvent for the amide-acid polyene product.

4. The method according to claim 3 wherein the anhydride-containing member is a dianhydride.

5. The method according to claim 3 wherein the anhydride-containing member is an acid anhydride.

6. The method according to claim 3 wherein the anhydride-containing member is an anhydride acid halide and the halide formed from reacting the anhydride acid halide with the ethylenically unsaturated alcohol is removed prior to reaction with the primary diamine.

7. The process of imidizing the amide-acid polyene of claim 1 which comprises heating said polyene at a temperature in the range 50°–250° C for a time sufficient to cause imidization.

8. The process according to claim 7 wherein the imidization is carried out in an inert solvent for the amide-acid polyene at a temperature in the range 50°–150° C.

9. A photocurable composition comprising
(A) an amide-acid containing polyene of the formula:

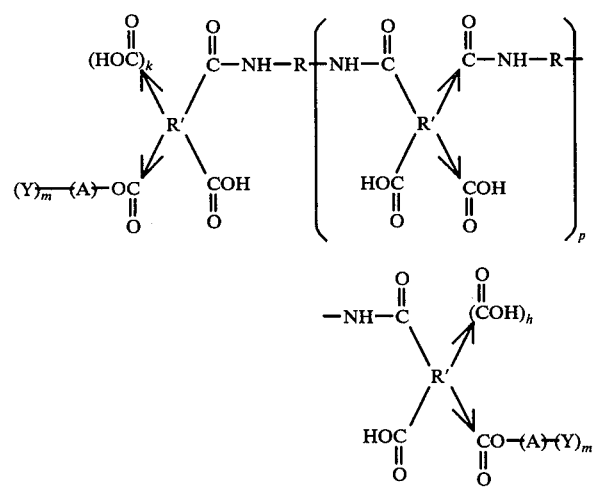

wherein → denotes isomerism, R is a divalent organic moiety remaining after a primary diamine has reacted to form amide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of —CR"=CH$_2$, —O—(CH$_2$)$_d$—CR"=CH$_2$ and

R" is hydrogen or methyl; $k$ and $h$ are 0 or 1; $m$ and $d$ are 1 to 10 and $p$ is 0 to 10, (B) a polythiol having a molecular weight in the range from about 94 to 20,000 of the general formula: R$_8$—(SH)$_n$ where $n$ is at least 2 and R$_8$ is a polyvalent organic moiety, the sum of $m$ and $n$ being greater than 3, the polyene/polythiol mole ratio being in the range 0.2 to 8.0:1, respectively, and (C) a photocuring rate accelerator.

10. A photocurable composition comprising
(A) an imide-containing polyene of the formula:

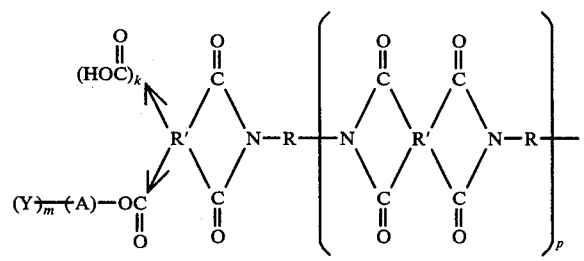

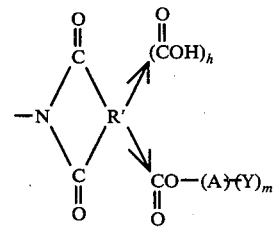

wherein → denotes isomerism, R is a divalent organic moiety remaining after a secondary diamide has reacted with adjacent carboxylic acid groups to form imide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of —CR"=CH$_2$, —O—(CH$_2$)$_d$—CR"=CH$_2$ and

R" is hydrogen or methyl; $k$ and $h$ are 0 or 1; $m$ and $d$ are 1 to 10 and $p$ is 0 to 10, (B) a polythiol having a molecular weight in the range from about 94 to 20,000 of the general formula: R$_8$—(SH)$_n$ where $n$ is at least 2 and R$_8$ is a polyvalent organic moiety, the sum of $m$ and $n$ being greater than 3, the polyene/polythiol mole ratio being in the range 0.2 to 8.0:1, respectively, and (C) a photocuring rate accelerator.

11. The process of forming a solid cured amide-acid containing polythioether which comprises admixing (A) a polyene of the formula:

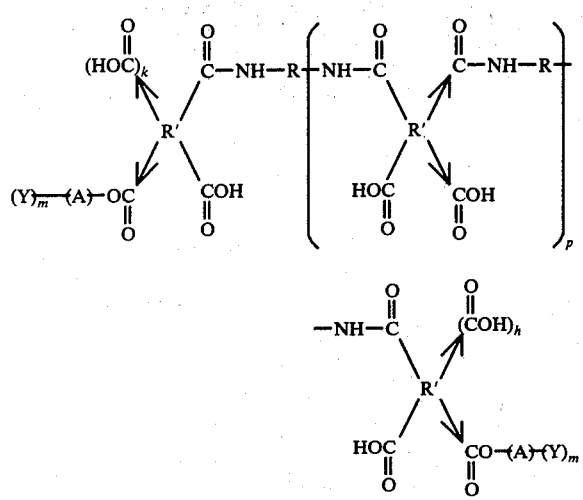

wherein → denotes isomerism, R is a divalent organic moiety remaining after a primary diamine has reacted to form amide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of $-CR''=CH_2$, $-O-(CH_2)_d-CR''=CH_2$ and $$-COCH_2CR''=CH_2;$$

R'' is hydrogen or methyl; $k$ and $h$ are 0 or 1; $m$ and $d$ are 1 to 10 and $p$ is 0 to 10, (B) a polythiol having a molecular weight in the range from about 94 to 20,000 of the general formula: $R_8-(SH)HD n$ where $n$ is at least 2 and $R_8$ is a polyvalent organic moiety, the sum of $m$ and $n$ being greater than 3, the polyene/polythiol mole ratio being in the range 0.2 to 8.0:1, respectively, and (C) a photocuring rate accelerator and, thereafter, exposing the mixture to actinic radiation.

12. The process of forming a solid cured imide containing polythioether which comprises admixing (A) a polyene of the formula:

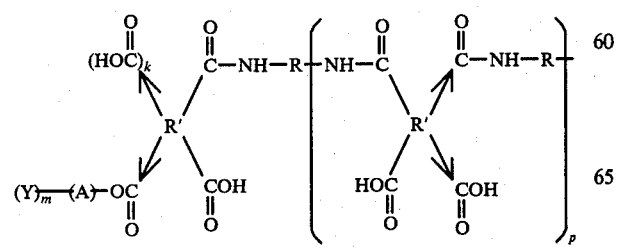

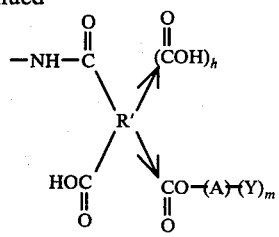

wherein → denotes isomerism, R is a divalent organic moiety remaining after a primary diamine has reacted to form amide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of $-CR''=CH_2$, $-O-(CH_2)_d-CH''=CH_2$ and

R'' is hydrogen or methyl; $k$ and $h$ are 0 or 1; $m$ and $d$ are 1 to 10 and $p$ is 0 to 10, (B) a polythiol having a molecular weight in the range from about 94 to 20,000 of the general formula: $R_8-(SH)_n$ where $n$ is at least 2 and $R_8$ is a polyvalent organic moiety, the sum of $m$ and $n$ being greater than 3, the polyene/polythiol mole ratio being in the range 0.2 to 8.0:1, respectively, and (C) a photocuring rate accelerator exposing said admixture to actinic radiation and, thereafter, heating the cured polythioether at a temperature in the range 50°–250° C for a time sufficient to imidize the amide-acid in the polyene.

13. The process of forming a solid cured imide containing polythioether which comprises admixing (A) a polyene of the formula:

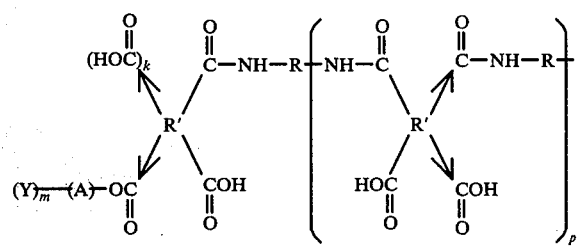

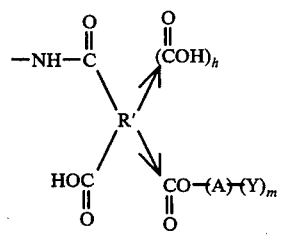

wherein → denotes isomerism, R is a divalent organic moiety remaining after a primary diamine has reacted to form amide linkages;

R' is an aromatic residue attached to at least 3 carbonyl groups at least two of which groups are attached to adjacent carbon atoms on the aromatic residue;

A is an alkylene group having 1 to 10 carbon atoms;

Y is a member of the group consisting of —CR"=CH$_2$, —O—(CH$_2$)$_d$—CR"=CH$_2$ and

R" is hydrogen or methyl; k and h are 0 or 1; m and d are 1 to 10 and p is 0 to 10, (B) a polythiol having a molecular weight in the range from about 94 to 20,000 of the general formula: R$_8$—(SH)$_n$ where n is at least 2 and R$_8$ is a polyvalent organic moiety, the sum of m and n being greater than 3, the polyene/polythiol mole ratio being in the range 0.2 to 8.0:1, respectively, and 0.01–5% by weight of (A) and (B) of a pinacol of the general formula:

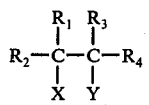

wherein R$_1$ and R$_3$ are members independently selected from the group consisting of substituted and unsubstituted aromatic radicals, R$_2$ and R$_4$ are members independently selected from the group consisting of substituted and unsubstituted aliphatic and aromatic radicals and X and Y are members independently selected from the group consisting of hydroxyl, alkoxy and aryloxy and, thereafter, heating the admixture in the range 50°–250° C.

14. The process of forming a solid cured imide containing polythioether which comprises admixing (A) an imide containing polyene of the formula:

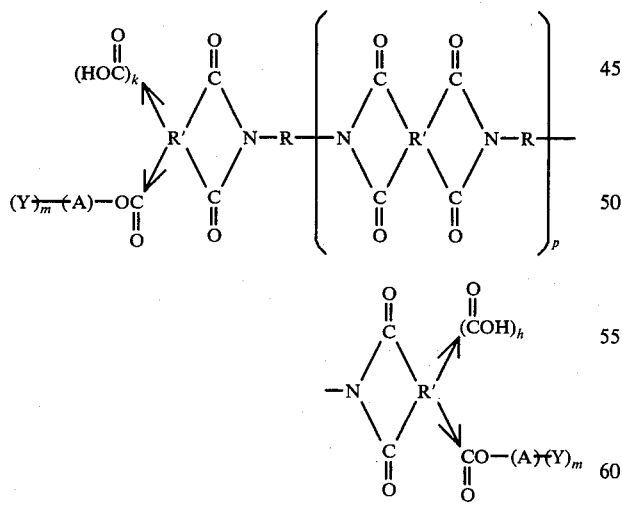

wherein → denotes isomerism, R is a divalent organic moiety remaining after a secondary diamide has reacted with adjacent carboxylic acid groups to form imide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of —CR"=CH$_2$, —O—(CH$_2$)$_d$—CR"=CH$_2$ and

R" is hydrogen or methyl; k and h are 0 or 1; m and d are 1 to 10 and p is 0 to 10, (B) a polythiol having a molecular weight in the range from about 94 to 20,000 of the general formula: R$_8$—(SH)$_n$ where n is at least 2 and R$_8$ is a polyvalent organic moiety, the sum of m and n being greater than 3, the polyene/polythiol mole ratio being in the range 0.2 to 8.0:1, respectively, and (C) a photocuring rate accelerator. and, thereafter, exposing the mixture to actinic radiation.

15. The process of forming a solid cured imide containing polythioether which comprises admixing (A) a polyene of the formula:

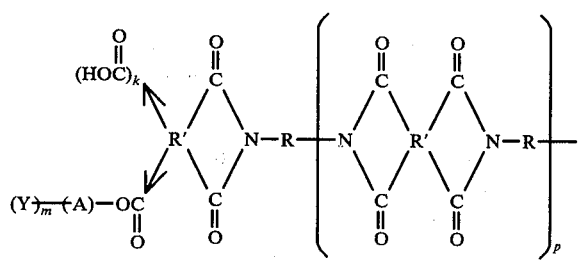

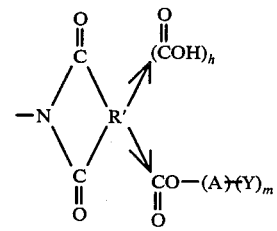

wherein → denotes isomerism, R is a divalent organic moiety remaining after a secondary diamide has reacted with adjacent carboxylic acid groups to form imide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of —CR"=CH$_2$, —O—(CH$_2$)$_d$—CR"=CH$_2$ and

R" is hydrogen or methyl; k and h are 0 or 1; m and d are 1 to 10 and p is 0 to 10, (B) a polythiol having a molecular weight in the range from about 94 to 20,000 of the general formula: R$_8$—(SH)$_n$ where n is at least 2 and R$_8$ is a polyvalent organic moiety, the sum of $m$ and $n$ being greater than 3, the polyene/polythiol mole ratio being in the range 0.2 to 8.0:1, respectively, and 0.01–5% by weight of (A) and (B) of a pinacol of the general formula:

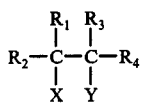

wherein $R_1$ and $R_3$ are members independently selected from the group consisting of substituted and unsubstituted aromatic radicals, $R_2$ and $R_4$ are members independently selected from the group consisting of substituted and unsubstituted aliphatic and aromatic radicals and X and Y are members independently selected from the group consisting of hydroxyl, alkoxy and aryloxy and, thereafter, heating the admixture in the range 50°–250° C.

16. The process of forming a solid cured imide containing polythioether which comprises admixing (A) a polyene of the formula:

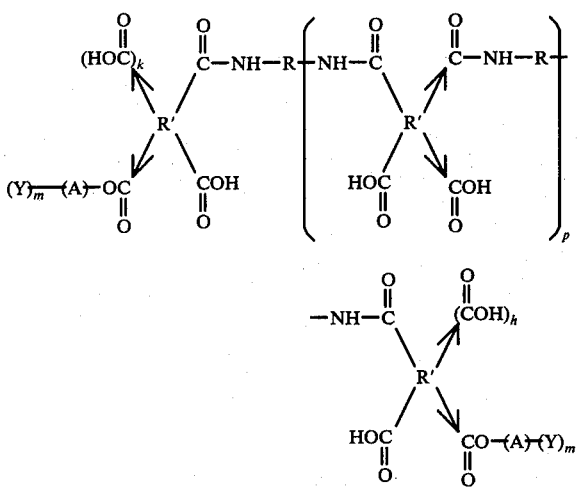

wherein → denotes isomerism, R is a divalent organic moiety remaining after a primary diamine has reacted to form amide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of $-CR''=CH_2$, $-O-(CH_2)_d-CR''=CH_2$ and

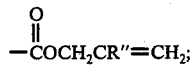

R'' is hydrogen or methyl; $k$ and $h$ are 0 or 1; $m$ and $d$ are 1 to 10 and $p$ is 0 to 10, (B) a polythiol having a molecular weight in the range from about 94 to 20,000 of the general formula: $R_8-(SH)_n$ where $n$ is at least 2 and $R_8$ is a polyvalent organic moiety, the sum of $m$ and $n$ being greater than 3, the polyene/polythiol mole ratio being in the range 0.2 to 8.0:1, respectively, and (C) a photocuring rate accelerator heating said admixture at a temperature in the range 50°–250° C for a time sufficient to imidize the amide-acid in the polyene and, thereafter, exposing said admixture to actinic radiation to form a cured imide containing polythioether.

17. An article comprising the composition of claim 9 as a coating on a substrate.

18. The article according to claim 17 wherein the substrate is an electrical conductor.

19. An article comprising the composition of claim 10 as a coating on a substrate.

20. The article of claim 19 wherein the substrate is an electrical conductor.

21. An article comprising a cured amide-acid containing polythioether as a coating on a substrate.

22. The article according to claim 21 wherein the substrate is an electrical conductor.

23. An article comprising a cured imide containing polythioether as a coating on a substrate.

24. The article according to claim 23 wherein the substrate is an electrical conductor.

25. The article according to claim 24 wherein the electrical conductor is a wire.

26. The process of coating a substrate which comprises applying to a substrate a curable composition comprising (A) an amide-acid containing polyene of the formula:

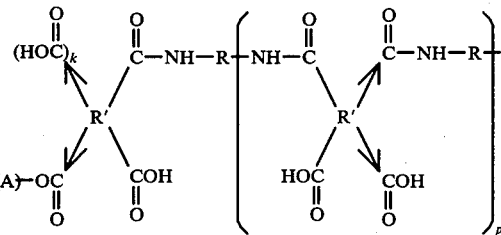

wherein → denotes isomerism, R is a divalent organic moiety remaining after a primary diamine has reacted to form amide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of $-CR''=CH_2$, $-O-(CH_2)_d-CR''=CH_2$ and

R" is hydrogen or methyl; $k$ and $h$ are 0 or 1; $m$ and $d$ are 1 to 10 and $p$ is 0 to 10, and (B) a polythiol having a molecular weight in the range from about 94 to 20,000 of the general formula: $R_8$—$(SH)_n$ where $n$ is at least 2 and $R_8$ is a polyvalent organic moiety, the sum of $m$ and $n$ being greater than 3, the polyene/polythiol mole ratio being in the range 0.2 to 8.0:1, respectively, exposing said curable composition under ambient conditions to a free radical generator to form a solidified, cured polythioether coating on said substrate and, thereafter heating said cured composition in the range 50°–250° C to imidize the polyene.

27. The process according to claim 26 wherein the curable composition contains 0.005 to 50% by weight of the polyene and polythiol of said curable composition of a photocuring rate accelerator and the free radical generator is actinic radiation.

28. The process according to claim 26 wherein the free radical generator is high energy ionizing radiation.

29. A process for forming a continuous flexible adherent cured coating on the surface of an electrical conductor selected from the group consisting of wire and cable which comprises immersing said electrical conductor in a bath of a liquid radiation curable composition comprising (A) an amide-acid containing polyene of the formula:

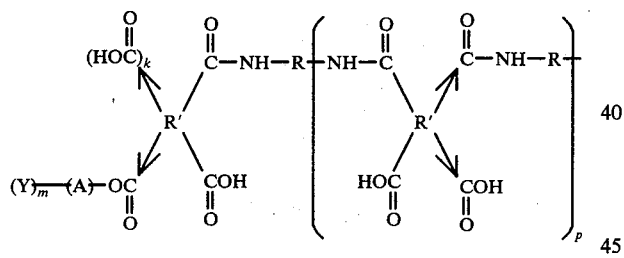

-continued

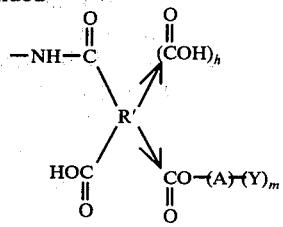

wherein → denotes isomerism, R is a divalent organic moiety remaining after a primary diamine has reacted to form amide linkages;

R' is an aromatic residue attached to at least 3 carbonyl groups at least two of which groups are attached to adjacent carbon atoms on the aromatic residue;

A is an alkylene group having from 1 to 10 carbon atoms;

Y is a member of the group consisting of —CR"=CH$_2$, —O—(CH$_2$)$_d$—CR"=CH$_2$ and

R" is hydrogen or methyl; $k$ and $h$ are 0 or 1; $m$ and $d$ are 1 to 10 and $p$ is 0 to 10, (B) a polythiol having a molecular weight in the range from about 94 to 20,000 of the general formula: $R_8$—$(SH)_n$ where $n$ is at least 2 and $R_8$ is a polyvalent organic moiety, the sum of $m$ and $n$ being greater than 3, the polyene/polythiol mole ratio being in the range 0.2 to 8.0:1, respectively, and (C) a photocuring rate accelerator, thus coating said electrical conductor with said composition, passing said coated electrical conductor through a die, exposing said coated electrical conductor to actinic radiation for a time sufficient to cure said coating on said electrical conductor under ambient conditions and, thereafter, heating said coated electrical conductor in the range 50°–250° C to imidize the polyene.

* * * * *

UNITED STATES PATENT AND TRADEMARK OFFICE
CERTIFICATE OF CORRECTION

PATENT NO. : 4,080,484

DATED : March 21, 1978

INVENTOR(S) : Eckart Mathias

It is certified that error appears in the above-identified patent and that said Letters Patent are hereby corrected as shown below:

In column 3, line 40, delete "$-CR''=CH_2-O-(CH_2)_d-CR''=CH_2$" and insert therefor --$CR''=CH_2-O-(CH_2)_d-CR''=CH_2$--.

In column 8, lines 5 and 6, delete "$HS-R_9-COOH$" and insert therefor --$HS-R_9-COOH$--.

In column 8, line 7, delete "$R_{10}\!-\!\!-\!OH)_n$" and insert therefor --$R_{10}\!-\!\!(OH)_n$--.

In column 12, line 25, delete "polyenepolythiol" and insert therefor --polyene-polythiol--.

In column 12, line 41, delete "polyenepolythiol" and insert therefor --polyene-polythiol--.

In column 22, line 26, delete "homgeneous" and insert therefor --homogeneous--.

In column 21, line 29, delete "imide" and insert therefor --amide--.

UNITED STATES PATENT AND TRADEMARK OFFICE
CERTIFICATE OF CORRECTION

PATENT NO. : 4,080,484
DATED : March 21, 1978
INVENTOR(S) : Eckart Mathias

It is certified that error appears in the above-identified patent and that said Letters Patent are hereby corrected as shown below:

In column 29, line 47, delete "$R_8-(SH)HD\ n$" and insert therefor --$R_8-(SH)_n$--.

In column 30, line 22, delete "$-CR"=CH_2,\ -O-(CH_2)_d-CH"=CH_2$" and insert therefor --$CR"=CH_2,\ -O-(CH_2)_d-CR"=CH_2$--.

In column 23, line 57, delete "cooled" and insert therefor -- coated --.

Signed and Sealed this

Twenty-eighth Day of November 1978

[SEAL]

Attest:

RUTH C. MASON
Attesting Officer

DONALD W. BANNER
Commissioner of Patents and Trademarks